US012583819B2

(12) United States Patent
Pai et al.

(10) Patent No.: US 12,583,819 B2
(45) Date of Patent: Mar. 24, 2026

(54) POLYTHIOL COMPOSITION, OPTICAL POLYMERIZABLE COMPOSITION, AND OPTICAL PRODUCT

(71) Applicant: SK pucore co., ltd., Ulsan (KR)

(72) Inventors: Jae Young Pai, Gyeonggi-do (KR); Jeong Moo Kim, Gyeonggi-do (KR); Hyuk Hee Han, Gyeonggi-do (KR); Jung Hwan Myung, Gyeonggi-do (KR); Kyeong Hwan You, Gyeonggi-do (KR); Joo Young Jung, Gyeonggi-do (KR); Myung Ok Kyun, Gyeonggi-do (KR); Ji Yeon Ryu, Gyeonggi-do (KR)

(73) Assignee: SK pucore co., ltd., Ulsan (KR)

( * ) Notice: Subject to any disclaimer, the term of this patent is extended or adjusted under 35 U.S.C. 154(b) by 598 days.

(21) Appl. No.: 18/044,206

(22) PCT Filed: Sep. 16, 2021

(86) PCT No.: PCT/KR2021/012676

§ 371 (c)(1),
(2) Date: Mar. 7, 2023

(87) PCT Pub. No.: WO2022/065802

PCT Pub. Date: Mar. 31, 2022

(65) Prior Publication Data

US 2024/0208899 A1 Jun. 27, 2024

(30) Foreign Application Priority Data

Sep. 22, 2020 (KR) ........................ 10-2020-0122399

(51) Int. Cl.

| | |
|---|---|
| ***C07C 321/06*** | (2006.01) |
| ***C07C 321/14*** | (2006.01) |
| ***C08G 18/12*** | (2006.01) |
| ***C08G 18/38*** | (2006.01) |
| ***C08G 18/72*** | (2006.01) |
| ***C08G 18/75*** | (2006.01) |
| ***C08G 18/83*** | (2006.01) |
| ***C08L 75/04*** | (2006.01) |
| ***G02B 1/04*** | (2006.01) |

(52) U.S. Cl.

CPC .......... *C07C 321/14* (2013.01); *C07C 321/06* (2013.01); *C08G 18/12* (2013.01); *C08G 18/3876* (2013.01); *C08G 18/72* (2013.01); *C08G 18/722* (2013.01); *C08G 18/758* (2013.01); *C08G 18/834* (2013.01); *C08L 75/04* (2013.01); *G02B 1/041* (2013.01)

(58) Field of Classification Search

CPC .... C08G 18/72; C08G 18/758; C08G 18/834; C08G 18/3876; C08G 18/722; C07C 321/06

See application file for complete search history.

(56) References Cited

U.S. PATENT DOCUMENTS

| | | | | |
|---|---|---|---|---|
| 2014/0327869 A1* | 11/2014 | Renzi | ..................... | G02B 1/041 528/80 |
| 2018/0072839 A1* | 3/2018 | Wu | ..................... | C08G 18/834 |
| 2018/0201718 A1* | 7/2018 | Kim | ..................... | C08G 18/7642 |

FOREIGN PATENT DOCUMENTS

| | | | |
|---|---|---|---|
| EP | 2075271 | A1 | 7/2009 |
| EP | 4209525 | A1 | 7/2023 |
| JP | 2004-182686 | A | 7/2004 |
| JP | 2018-024588 | A | 2/2018 |
| KR | 10-0180926 | B1 | 5/1999 |
| KR | 10-2013-0050262 | A | 5/2013 |
| KR | 10-1338568 | B1 | 12/2013 |
| KR | 10-2014-0125457 | A | 10/2014 |
| KR | 10-2017-0065821 | A | 6/2017 |
| KR | 10-2018-0089363 | A | 8/2018 |
| KR | 10-1961941 | B1 | 3/2019 |
| KR | 10-2019-0036837 | A | 4/2019 |
| KR | 10-2019-0086418 | A | 7/2019 |
| KR | 10-2001495 | B1 | 7/2019 |
| KR | 20190138145 | A | 12/2019 |
| KR | 10-2077653 | B1 | 2/2020 |
| KR | 10-2020-0026853 | A | 3/2020 |
| KR | 10-2122703 | B1 | 6/2020 |
| KR | 10-2150590 | B1 | 9/2020 |
| WO | 2013069964 | A1 | 5/2013 |
| WO | 2019-189761 | A1 | 10/2019 |

OTHER PUBLICATIONS

Extended European Search Report for the European Patent Application No. 21872830.1 issued by the European Patent Office on Sep. 16, 2024.

Office Action for Chinese Patent Application No. 202180063797.8 issued by the Chinese Patent Office on Jun. 11, 2025.

Dong Gyu Jang et al., Synthesis of ultra-high refractive monomer for plastic spectacle lenses and manufacture of spectacle lenses using the same, Sep. 2008, pp. 1-6, vol. 13, No. 3, J. Korean Oph. Opt. Soc.

International Search Report for the International Application No. PCT/KR2021/012676 issued by the Korean Patent Office on Dec. 27, 2021.

(Continued)

*Primary Examiner* — Michael L Leonard

(74) *Attorney, Agent, or Firm* — IP & T GROUP LLP

(57) ABSTRACT

A polythiol composition according to exemplary embodiments includes a first polythiol compound and a second polythiol compound having a molecular weight greater than that of the first polythiol compound and the number of functional groups greater than or equal to the number of functional groups of the first polythiol compound. A content of the second polythiol compound is 500 ppm to 20,000 ppm based on a weight of the first polythiol compound. The reaction rate of an isocyanate-based compound may be controlled through the second polythiol compound, thus to suppress a stria phenomenon and improve mechanical properties of an optical product.

15 Claims, No Drawings

(56) References Cited

OTHER PUBLICATIONS

Office Action for the Korean Patent Application No. 10-2020-0122399 issued by the Korean Intellectual Property Office on Feb. 22, 2022.
Notice of Allowance for the Korean Patent Application No. 10-2020-0122399 issued by the Korean Intellectual Property Office on Aug. 22, 2022.

* cited by examiner

POLYTHIOL COMPOSITION, OPTICAL POLYMERIZABLE COMPOSITION, AND OPTICAL PRODUCT

This application is a national stage application of PCT/KR2021/012676 filed on Sep. 16, 2021, which claims priority of Korean patent application number 10-2020-0122399 filed on Sep. 22, 2020. The disclosure of each of the foregoing applications is incorporated herein by reference in its entirety.

This application claims priority to Korean Patent Application No. 10-2020-0122399 filed on Sep. 22, 2020 in the Korean Intellectual Property Office (KIPO), the entire disclosure of which is incorporated by reference herein.

BACKGROUND

1. Field

The present invention relates to a polythiol composition, an optical polymerizable composition ("polymerizable composition for an optical material"), and an optical product. More particularly, the present invention relates to a polythiol composition including a plurality of thiol-based compounds, a polymerizable composition for an optical material including the polythiol composition, and an optical product manufactured using the polymerizable composition.

2. Description of the Related Art

A polythiol compound is widely used, for example, as a raw material for manufacturing a polyurethane resin. For example, a polythiol compound is used to manufacture an optical lens using a polyurethane resin, and quality such as purity of the polythiol compound as a raw material may directly affect the quality of the optical lens.

For example, a polythiourethane-based compound prepared by reacting a polythiol compound and an isocyanate compound may be used as a base material of the optical lens.

For example, Korean Patent Laid-Open Publication No. 10-1338568 discloses a method for synthesizing a polythiol compound by reacting a polyol compound with thiourea to prepare an isothiouronium salt, and then hydrolyzing it using aqueous ammonia.

Depending on the reactivity of the synthesized polythiol compound with the isocyanate compound, a transparency of the lens may be reduced or optical non-uniformity may be caused. In addition, mechanical and optical properties of the lens may be varied depending on physical properties such as molecular weight, the number of functional groups, and the like of the polythiol compound.

SUMMARY

An object according to exemplary embodiments is to provide a polythiol composition with improved reaction properties and optical properties.

In addition, another object according to exemplary embodiments is to provide a polymerizable composition for an optical material including the polythiol composition with improved reaction characteristics and optical properties.

Further, another object according to exemplary embodiments is to provide an optical product manufactured of the polymerizable composition for an optical material.

A polythiol composition according to exemplary embodiments includes: a first polythiol compound: and a second polythiol compound which has a molecular weight greater than that of the first polythiol compound and the number of functional groups greater than or equal to the number of functional groups of the first polythiol compound. A content of the second polythiol compound is 500 to 20,000 ppm based on a weight of the first polythiol compound.

In some embodiments, the first polythiol compound may include a trifunctional polythiol compound, and the second polythiol compound may include a tetrafunctional polythiol compound.

In some embodiments, the first polythiol compound may include at least one selected from the group consisting of a trifunctional polythiol compound represented by Formula 1 below and tetrafunctional polythiol compounds represented by Formulae 2-1 to 2-3 below:

[Formula 1]

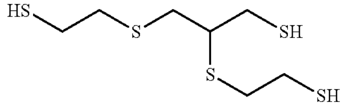

[Formula 2-1]

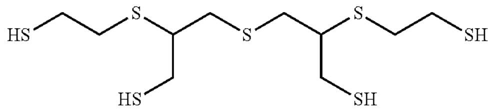

[Formula 2-2]

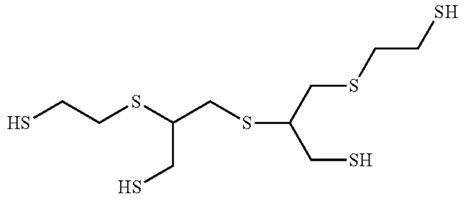

[Formula 2-3]

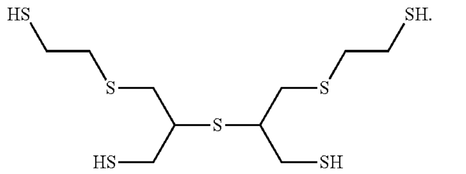

In some embodiments, the second polythiol compound may include a compound represented by $C_{12}H_{26}S_8$.

In some embodiments, the second polythiol compound may include at least one of a compound represented by Formula 3-1 below and a compound represented by Formula

[Formula 3-1]

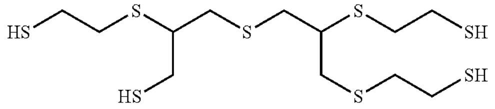

[Formula 3-2]

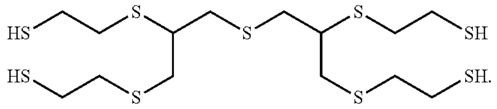

In some embodiments, the second polythiol compound may include the compound represented by Formula 3-1 and the compound represented by Formula 3-2 in a content of 500 to 10,000 ppm, respectively.

In some embodiments, a content of the second polythiol compound may be 1,000 to 20,000 ppm.

A polymerizable composition for an optical material according to exemplary embodiments includes: a first polythiol compound; a second polythiol compound which has a molecular weight greater than that of the first polythiol compound and the number of functional groups greater than or equal to the number of functional groups of the first polythiol compound; and an isocyanate-based compound. A content of the second polythiol compound is 500 to 20,000 ppm based on a weight of the first polythiol compound.

In some embodiments, the second polythiol compound may include a compound represented by $C_{12}H_{26}S_8$.

In some embodiments, the second polythiol compound may include at least one of a compound represented by Formula 3-1 below and a compound represented by Formula 3-2 below:

[Formula 3-1]

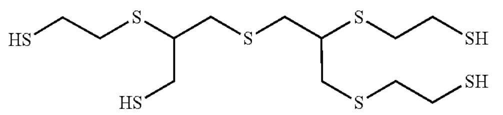

[Formula 3-2]

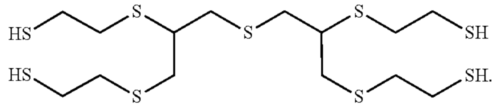

In some embodiments, the first polythiol compound may include a trifunctional polythiol compound.

In some embodiments, the first polythiol compound may include a compound represented by Formula 1 below:

[Formula 1]

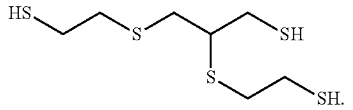

According to exemplary embodiments, there is provided an optical product including a polythiourethane resin in which a polythiol compound and an isocyanate-based compound are polymerized. The polythiol compound includes a first polythiol compound; and a second polythiol compound which has a molecular weight greater than that of the first polythiol compound and the number of functional groups greater than or equal to the number of functional groups of the first polythiol compound. A content of the second polythiol compound is 500 to 20,000 ppm based on a weight of the first polythiol compound.

In some embodiments, wherein the second polythiol compound may include a compound represented by $C_{12}H_{26}S_8$.

In some embodiments, the optical product may have a refractive index of 1.56 to 1.78.

According to the above-described embodiments, the polythiol composition may include a first polythiol compound and a second polythiol compound. The second polythiol compound may have a molecular weight greater than that of the first polythiol compound and the number of functional groups greater than or equal to the number of functional groups of the first polythiol compound.

As the second polythiol compound is added in a small amount, a reaction rate by the first polythiol compound may be reduced to prevent a stria phenomenon due to excessive flowability during manufacturing a lens. In addition, an overall glass transition temperature of the polythiol composition is increased through the second polythiol compound, such that mechanical properties of the lens may also be improved.

In some embodiments, the first polythiol compound may include a trifunctional polythiol compound, and the second polythiol compound may include a tetrafunctional polythiol compound. Therefore, the reactivity of the trifunctional polythiol compound may be appropriately controlled, thus to obtain a highly reliable lens supplemented with mechanical and optical properties.

DETAILED DESCRIPTION OF THE EMBODIMENTS

Hereinafter, embodiments of the present application will be described in detail. In this regard, the present invention may be altered in various ways and have various embodiments, such that specific embodiments will be illustrated in the drawings and described in detail in the present disclosure. However, the present invention is not limited to the specific embodiments, and it will be understood by those skilled in the art that the present invention is to cover all modifications, equivalents, and alternatives falling within the spirit and scope of the present invention.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to one aspect of the present application, there is provided a polythiol composition including a plurality of polythiol compounds. The polythiol composition may include a first polythiol compound and a second polythiol compound.

The first polythiol compound may include a polythiol compound serving as a base material in the polythiol composition or a polymerizable composition for an optical material to be described below. The first polythiol compound may be included in the polythiol composition as a main polythiol compound thereof.

The first polythiol compound may include a trifunctional polythiol compound and/or a tetrafunctional polythiol compound.

Non-limiting examples of the trifunctional polythiol compound may include a compound represented by $C_7H_{16}S_5$. In one embodiment, the trifunctional polythiol compound may include a compound represented by Formula 1 below.

[Formula 1]

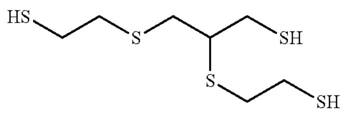

The trifunctional polythiol compound may be synthesized from, for example, a polyol compound obtained through a reaction with 2-mercaptoethanol and epihalohydrin.

After the polyol compound is reacted with thiourea under acidic conditions to produce a thiuronium salt, a trifunctional polythiol compound may be prepared through hydrolysis under basic conditions.

The synthesis process of the trifunctional polythiol compound may be exemplified by Scheme 1 below.

[Scheme 1]

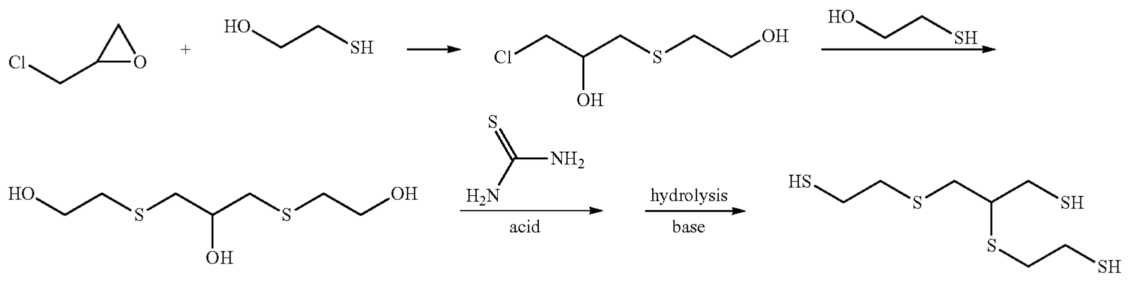

According to one embodiment, in the reaction step of epihalohydrin and 2-mercaptoethanol for synthesizing a trifunctional polythiol compound, a metal-containing catalyst such as sodium hydroxide or potassium hydroxide may be used.

The tetrafunctional polythiol compound may include, for example, a compound represented by $C_{10}H_{22}S_7$. Non-limiting examples of the tetrafunctional polythiol compound may include compounds represented by Formulae 2-1 to 2-3 below.

[Formula 2-1]

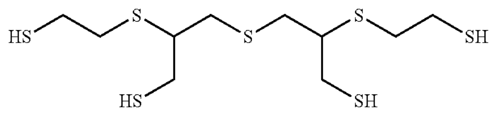

[Formula 2-2]

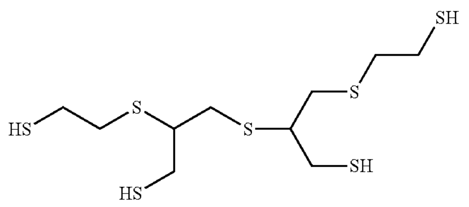

-continued

[Formula 2-3]

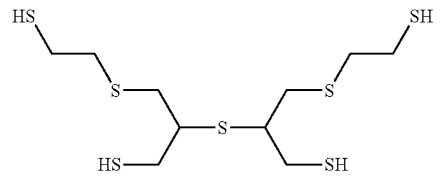

The tetrafunctional polythiol compound may be synthesized from, for example, a polyol compound obtained through a reaction with 2-mercaptoethanol and epihalohydrin.

The polyol compound may be reacted with a metal sulfide to produce a tetrafunctional polyol intermediate. After the tetrafunctional polyol intermediate is reacted with thiourea under acidic conditions to produce a thiuronium salt, a tetrafunctional polythiol compound may be prepared by hydrolysis under basic conditions.

The above synthesis process of the tetrafunctional polythiol compound may be exemplified by Scheme 2 below.

[Scheme 2]

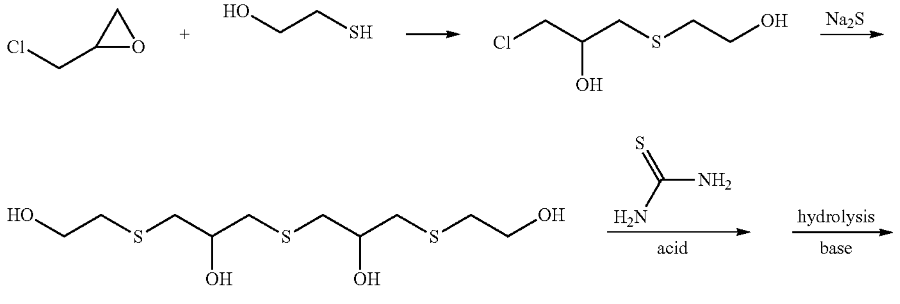

-continued

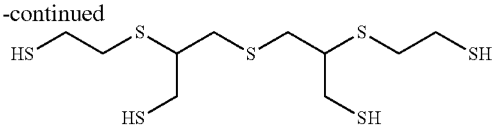

In one embodiment, a basic catalyst may be used in the reaction step of epihalohydrin and 2-mercaptoethanol for synthesizing a tetrafunctional polythiol compound. Examples of the basic catalyst may include tertiary amines such as triethyl amine, quaternary ammonium salts, triphenylphosphine, and trivalent chromium-based compounds.

As exemplified in Schemes 1 and 2 above, epichlorohydrin may be used as epihalohydrin. For example, a content of 2-mercaptoethanol may be 0.5 to 3 moles, preferably 0.7 to 2 moles, and more preferably 0.9 to 1.1 moles based on 1 mole of epihalohydrin. The basic catalyst may be used in an amount of 0.001 to 0.1 mol, and preferably 0.01 to 0.1 mol based on 1 mol of epihalohydrin.

In Schemes 1 and 2, reflux under acidic conditions may be used to generate an isothiouronium salt through a reaction with thiurea. In order to form such acidic conditions, acidic compounds such as hydrochloric acid, hydrobromic acid, iodic acid, sulfuric acid, phosphoric acid, and the like may be used. The reflux temperature may be 90 to 120° C., preferably 100 to 120° C., and the reflux may be performed for about 1 to 10 hours, preferably 2 to 6 hours.

As described above, after generating the isothiuronium salt, a trifunctional or tetrafunctional polythiol compound may be prepared by hydrolysis under basic conditions. For example, it can be hydrolyzed by adding a basic aqueous solution to a reactive solution containing the isothiouronium salt.

In one embodiment, the reaction solution containing the isothiouronium salt is cooled to a temperature of 20 to 60° C., preferably 25 to 55° C., and more preferably 25 to 50° C. Thereafter, the basic aqueous solution may be added.

In some embodiments, the basic aqueous solution may include a strong basic compound, for example, alkali metal hydroxide, alkaline earth metal hydroxide and/or alkali metal hydride, such as NaOH, KOH, LiOH, $Ca(OH)_2$, LiH, NaH, etc.

According to exemplary embodiments, an organic solvent may be added before adding the basic aqueous solution. An organic solvent having low reactivity or substantially no reactivity and a boiling point exceeding a thiolation reaction temperature may be used so as to allow a thiolation reaction to proceed stably.

Examples of the organic solvent may include toluene, xylene, chlorobenzene, and dichlorobenzene. Preferably, toluene may be used in consideration of reaction stability and toxicity from an organic solvent.

The polythiol-based compound obtained as described above may be further purified. For example, by repeatedly performing acid washing and water washing processes, impurities included in the polythiol-based compound may be removed, in addition, the transparency of the optical material prepared from the polythiol composition may be improved. Thereafter, drying, filtration, etc. may be additionally performed.

In one embodiment, an aqueous layer may be separated or removed through layer separation after proceeding with the hydrolysis. Acid washing may be carried out at a temperature of about 20 to 50° C., and preferably about 30 to 40° C. for 20 minutes to 1 hour, or 20 minutes to 40 minutes by introducing an acid solution to the obtained organic phase solution.

After the acid washing, a water washing process may be conducted by adding degassed water having a dissolved oxygen concentration adjusted to 5 ppm or less, preferably 3 ppm or less, and more preferably 2 ppm or less. The water washing process may be conducted at a temperature of about 20 to 50° C., preferably about 35 to 45° C. for 20 minutes to 1 hour, or 20 minutes to 40 minutes. The water washing process may be repeated two or more times, for example, may be conducted 3 to 6 times.

After the acid washing and water washing process, the residual organic solvent and moisture may be removed by heating under reduced pressure, followed by filtering through a filter to obtain a polythiol-based compound with high purity.

In preferred embodiments, as the first polythiol compound, a trifunctional polythiol compound may be used. The trifunctional polythiol compound may be advantageous in terms of economic advantages and easiness of processing due to low viscosity.

The polythiol composition according to exemplary embodiments may further include a second polythiol compound. The second polythiol compound may be included or added as a regulator of the reactivity or reaction rate for the polythiol composition.

In one embodiment, the second polythiol compound may include a polythiol compound having a higher molecular weight than that of the first polythiol compound. In one embodiment, the second polythiol compound may include a polythiol compound having the number of functional groups greater than or equal to the number of functional groups (the number of thiol groups) of the first polythiol compound.

In some embodiments. the second polythiol compound may include a compound represented by $C_{12}H_{26}S_8$. In some embodiments, the second polythiol compound may include a tetrafunctional thiol compound represented by Formula 3-1 and/or Formula 3-2 below.

[Formula 3-1]

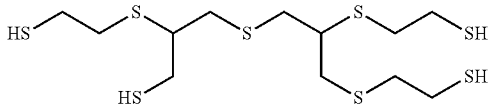

[Formula 3-2]

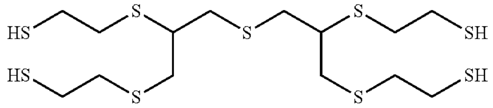

In one embodiment, the compound of Formula 3-1 or the compound of Formula 3-2 may be used alone as the second polythiol compound. In one embodiment, the compound of Formula 3-1 or the compound of Formula 3-2 may be used in combination as the second polythiol compound.

The second polythiol compound may have a greater molecular weight or number of carbon atoms than that of the first polythiol compound. Thereby, an excessive increase in reaction rate of the polythiol composition or the first polythiol compound with an isocyanate-based compound to be described below may be inhibited through the second polythiol compound.

As described above, when using the trifunctional polythiol compound as the first polythiol compound, it may be advantageous in terms of economic advantages and easiness of processing. However, due to a fast reaction rate of the trifunctional polythiol compound, a generation of stria in the lens may be caused. In addition, due to the relatively high flowability and low glass transition temperature (Tg) of the trifunctional polythiol compound, mechanical properties of optical products such as a lens may also be reduced.

However, according to exemplary embodiments, as the second polythiol compound having a relatively large molecular weight, number of functional groups, and number of carbon atoms is mixed together as a reaction regulator, an excessive increase in reaction rate of the trifunctional polythiol compound may be inhibited, and the overall glass transition temperature of the optical product such as a lens manufactured from the polythiol composition may be increased.

For example, as the second polythiol compound which is a tetrafunctional compound having a large chain length is added, the intermolecular bond and interaction of the first polythiol compounds may be buffered or controlled, and for example, an excessive increase in reactivity of the trifunctional polythiol compound may be alleviated.

In addition, as the second polythiol compound having a large molecular weight is added, the glass transition temperature (Tg) of the optical product may be increased through an increase in intermolecular attraction and interaction, and heat resistance may also be enhanced.

Therefore, it is possible to obtain an optical product in which all the economic advantages, easiness of processing, optical properties and mechanical properties are improved in a well-balanced manner.

In some embodiments, as the first polythiol compound, the above-described tetrafunctional polythiol compound may be used. In this case, as the second polythiol compound having a relatively higher molecular weight, number of functional groups, and number of carbon atoms than those of the tetrafunctional polythiol compound is mixed together, the above-described effects may be substantially obtained similar thereto.

According to exemplary embodiments, the second polythiol compound may be included in a range of about 500 to 20,000 ppm based on a weight of the first polythiol compound. Within the above range, it is possible to prevent an excessive decrease in reaction rate and coloration/white turbidity of the lens while sufficiently implementing effects of inhibiting the reaction rate and increasing the glass transition temperature through the second polythiol compound.

Preferably, the content of the second polythiol compound may be 1,000 to 20,000 ppm. More preferably, the content of the second polythiol compound may be 10,000 to 20,000 ppm.

In a preferred embodiment. the second polythiol compound may include the compound of Formula 3-1 and the compound of Formula 3-2 together. In this case, the compound of Formula 3-1 and the compound of Formula 3-2 may be included in a content of about 500 to 10,000 ppm, and more preferably about 5,000 to 10,000 ppm, respectively.

For example, when the compound of Formula 3-2 having a relatively high molecular weight and number of carbon atoms is used together with the compound of Formula 3-1, an appropriate reaction rate may be maintained while preventing an excessive increase in reaction rate and white turbidity phenomenon.

In addition, according to another aspect of the present application, there is provided a polymerizable composition for an optical material including the above-described polythiol composition.

The polymerizable composition for an optical material may include the polythiol composition and an isocyanate-based compound. Alternatively, the polymerizable composition for an optical material may include the above-described first polythiol compound, second polythiol compound, and isocyanate-based compound.

The isocyanate-based compound may include a compound that is useable as a monomer for synthesizing polythiourethane. In a preferred embodiment, the isocyanate-based compound may include 1,3-bis(isocyanatomethyl) cyclohexane, hexamethylene diisocyanate, isophorone diisocyanate, xylene diisocyanate, toluene diisocyanate and the like. These may be used alone or in combination of two or more thereof.

The polymerizable composition for an optical material may further include additives such as a release agent, a reaction catalyst, a thermal stabilizer, an ultraviolet absorber, a bluing agent and the like.

Examples of the release agent may include a fluorine-based nonionic surfactant having a perfluoroalkyl group, a hydroxyalkyl group or a phosphoric acid ester group: a silicone-based nonionic surfactant having a dimethylpolysiloxane group, a hydroxyalkyl group or a phosphoric acid ester group; alkyl quaternary ammonium salts such as trimethylcetyl ammonium salt, trimethylstearyl, dimethylethylcetyl ammonium salt, triethyldodecyl ammonium salt, trioctylmethyl ammonium salt and diethylcyclohexadodecyl ammonium salt; acidic phosphoric acid ester and the like. These may be used alone or in combination of two or more thereof.

As the reaction catalyst, a catalyst used in the polymerization reaction of the polythiourethane resin may be used. For example, dialkyltin halide catalysts, such as dibutyltin dichloride and dimethyltin dichloride; dialkyltin dicarboxylate catalysts such as dimethyltin diacetate, dibutyltin dioctanoate, and dibutyltin dilaurate; dialkyltin dialkoxide catalysts such as dibutyltin dibutoxide and dioctyltin dibutoxide; dialkyltin dithio alkoxide catalysts such as dibutyltin di(thiobutoxide); dialkyltin oxide catalysts such as di(2-ethylhexyl)tin oxide, dioctyltin oxide, and bis(butoxydibutyltin) oxide; dialkyltin sulfide catalysts, and the like may be used. These may be used alone or in combination of two or more thereof.

As examples of the ultraviolet absorber, benzophenone-based, benzotriazole-based, salicylate-based, cyanoacrylate-based, oxanilide-based compounds, and the like may be used. As examples of the thermal stabilizer, metal fatty acid salt-based, phosphorus-based, lead-based, organotin-based compounds, and the like may be used. These may be used alone or in combination of two or more thereof.

The bluing agent may be included as a color regulator of the optical material prepared from the polythiourethane resin. For example, the bluing agent may have an absorption band in a wavelength band from orange to yellow in a visible light region.

Examples of the bluing agent may include a dye, a fluorescent whitening agent, a fluorescent pigment, an inorganic pigment, and the like, and may be appropriately selected according to physical properties or resin color required for the optical product to be manufactured. When a dye is used as the bluing agent, for example, a dye having a maximum absorption wavelength of 520 to 600 nm, and preferably 540 to 580 nm may be used. Preferably, anthraquinone-based dyes may be used.

A polythiourethane resin may be produced through a polymerization reaction of the polythiol compound included in the polythiol composition with the isocyanate-based compound, and the polymerization reaction rate may be adjusted or controlled through the reaction control action of the second polythiol compound included in the polythiol composition.

Accordingly. it is possible to prevent yellowing or white turbidity phenomenon, inhibit the generation of stria, and manufacture an optical product in which uniform and improved optical properties are maintained for a long period of time.

In some embodiments, based on a total weight of the polymerizable composition for an optical material, the polythiol-based compound may be included in a content of about 40 to 60% by weight ("wt. %") and the isocyanate-based compound may be included in a content of about 40 to 60 wt. %, while the additive may be included in a content of about 0.01 to 1 wt. %. As described above, the second polythiol compound may be included in a range of about 500 to 20,000 ppm based on the weight of the first polythiol compound.

In some embodiments, the reaction rate of the polymerizable composition for an optical material included in Equation 1 to be described below may be appropriately controlled by the second polythiol compound.

In one embodiment, when the trifunctional polythiol compound is used as the first polythiol compound, the reaction rate may be 0.20 to 0.35, preferably 0.24 to 0.35, and more preferably 0.24 to 0.30. In one embodiment, when the tetrafunctional polythiol compound is used as the first polythiol compound, the reaction rate may be 0.20 or less.

As described above, the second polythiol compound may be included in the polythiol composition to be included in the polymerizable composition for an optical material together. In one embodiment, the second polythiol compound may be added to a composition containing the isocyanate-based compound to be included in the polymerizable composition for an optical material. In one embodiment, the second polythiol compound may be mixed with the polythiol-based compound and the isocyanate-based compound together to be included in the polymerizable composition for an optical material.

Further, according to another aspect of the present application, there may be provided an optical product manufactured using the above-described polymerizable composition for an optical material.

For example, after degassing the polymerizable composition for an optical material under reduced pressure, the resultant composition may be injected into a mold for molding an optical material. Mold injection may be performed, for example, in a temperature range of 20 to 40° C., and preferably 20 to 35° C.

After the mold injection, the temperature may be gradually increased, thereby allowing a polymerization reaction of the polythiourethane resin to proceed. The polymerization temperature may range from 20 to 150° C., and preferably 25 to 125° C. For example, the maximum polymerization temperature may range from 100 to 150° C., preferably 110 to 140° C., and more preferably 115 to 130° C.

The temperature increase rate may be 1 to 10° C./min, preferably 3 to 8° C./min, and more preferably 4 to 7° C./min. The polymerization time may be 10 to 20 hours, and preferably 15 to 20 hours.

For example, a lens having uniform optical properties and mechanical properties can be easily obtained by appropriately controlling the reaction rate within the above temperature range.

After completion of polymerization, the polymerized polythiourethane resin may be separated from the mold to obtain an optical product. In one embodiment, after separation from the mold, a curing process may be further conducted. The curing process may be conducted in a range of 100 to 150° C., preferably 110 to 140° C., more preferably 115 to 130° C. for about 1 to 10 hours, preferably 2 to 8 hours, and more preferably 3 to 6 hours.

The optical product may be manufactured in the form of a spectacle lens, a camera lens, a light emitting diode, etc. according to a shape of the mold.

The refractive index of the optical product may be adjusted according to the type and/or content ratio of the polythiol-based compound and the isocyanate-based compound used in the polymerizable composition for an optical material. For example, the refractive index of the optical product may be adjusted in a range of 1.56 to 1.78, 1.58 to 1.76. 1.60 to 1.78, or 1.60 to 1.76, and preferably in a range of 1.65 to 1.75 or 1.69 to 1.75.

As described above, the glass transition temperature (Tg) and heat resistance of an optical product may be increased through the second polythiol compound included in the polythiol composition. In some embodiments, the glass transition temperature of the optical product may be 90 to 110° C. Preferably, the glass transition temperature of the optical product may be 92 to 106° C., and more preferably 93 to 106° C., 94 to 106° C., or 95 to 106° C.

The optical product may be improved by further conducting surface treatment such as anti-fouling, color imparting, hard coat, surface polishing, hardness strengthening and the like.

Hereinafter, embodiments provided in the present application will be further described with reference to specific experimental examples. However, the following experimental examples only illustrate the present invention and are not intended to limit the appended claims, and those skilled in the art will obviously understand that various alterations and modifications are possible within the scope and spirit of the present invention. Such alterations and modifications are duly included in the appended claims.

PREPARATIVE EXAMPLES

1) Preparative Example 1: Synthesis of Trifunctional Polythiol Compound

Into a reactor, 200 parts by weight ("wt. parts") of 2-mercaptoethanol, 200 wt. parts of degassed water (dissolved oxygen concentration of 2 ppm), and 61.4 wt. parts of sodium hydroxide were added. In the reactor, 118.4 wt. parts of epichlorohydrin was slowly added dropwise at 9° C. to 13° C. and stirred for 3 hours.

Then, 360.5 wt. parts of thiourea and 666.8 wt. parts of hydrochloric acid having a purity of 36% were added, and stirred for 3 hours while refluxing at 110° C., such that a thiuronium chloride reaction was proceeded.

After cooling the obtained reaction solution to 45° C. 589.7 wt. parts of toluene was added and cooled to 26° C. again, and 829 wt. parts of 33 wt. % sodium hydroxide was added over 25 minutes at 25° C. to 45° C., followed by conducting hydrolysis at 40° C. to 60° C. for 3 hours.

Then, after performing layer separation for 1 hour, the aqueous layer was discarded, 234 wt. parts of 36% hydrochloric acid was added to the obtained toluene solution, and acid washing was conducted once at 33° C. to 40° C. for 30 minutes. After acid washing, 530 wt. parts of degassed water (dissolved oxygen concentration of 2 ppm) was added, and washing was conducted 4 times at 35° C. to 45° C. for 30 minutes, respectively. After removing toluene and residual moisture under heating and reduced pressure, 260 wt. parts of the trifunctional polythiol compound represented by Formula 1 was obtained by filtration under reduced pressure through a PTFE type membrane filter.

2) Preparative Example 2: Synthesis of Tetrafunctional Polythiol Compound

After introducing 60.0 wt. parts of water, 0.3 wt. parts of triethylamine and 73.0 wt. parts of 2-mercaptoethanol into a reactor, a temperature of the reactor was lowered to 0° C., and 88.2 wt. parts of epichlorohydrin was slowly added dropwise at a temperature of 15° C. or lower, and then further stirred at 30° C. for 3 hours. 145.8 wt. parts of 25% aqueous sodium sulfide solution was slowly added dropwise at 20° C. to 25° C., followed by stirring for additional 3 hours.

Then, 473.2 wt. parts of 36% hydrochloric acid and 177.8 wt. parts of thiourea were introduced, and stirred for 3 hours while refluxing at 110° C., such that a thiuronium chloride reaction was proceeded.

After the obtained reaction solution was cooled to 50° C., 305.6 wt. parts of toluene and 332.6 wt. parts of 50% NaOH were added, and then hydrolysis was conducted at 40° C. to 60° C. for 3 hours.

Then, the water layer was discarded after performing layer separation for 1 hour, and 120 wt. part of 36% hydrochloric acid was added to the obtained toluene solution, followed by acid washing once at 33° C. to 40° C. for 30 minutes. After acid washing, 250 wt. parts of degassed water (dissolved oxygen concentration of 2 ppm) was added, and washing was conducted 4 times at 35° C. to 45° C. for 30 minutes, respectively. After removing toluene and residual moisture under heating and reduced pressure, it was filtered under reduced pressure through a PTFE type membrane filter thus to obtain 140 wt. parts of the tetrafunctional polythiol compound represented by the above Formula 2-1.

Examples and Comparative Examples

Polythiol compositions of examples and comparative examples were prepared by adding a compound of Formula 3-1 below (Compound (A)) and/or a compound of Formula 3-2 (Compound (B)) as a second polythiol compound in the contents described in Table 1 compared to the trifunctional or tetrafunctional polythiol compound (first polythiol compound) prepared as described above.

[Formula 3-1] Compound (A)

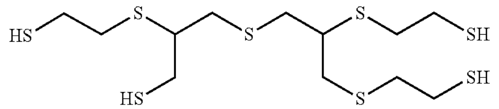

[Formula 3-2] Compound (B)

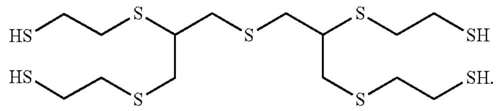

Preparation of Polymerizable Composition for an Optical Material and Manufacturing of Lens 1) The polythiol compositions of the examples and comparative examples were received so as to contain 48.0 wt. parts of the trifunctional polythiol of Preparative Example 1. Then, the received composition was uniformly admixed with 52.0 wt. parts of xylene diisocyanate, 0.012 wt. parts of dibutyltin chloride and 0.1 wt. parts of phosphoric acid ester release agent produced by ZELEC® UN tepan. Thereafter, a defoaming process was conducted at 600 Pa for 1 hour to prepare a polymerizable composition for an optical material.

Then, the composition filtered through a 3 μm Teflon filter was injected into a mold provided with a glass mold and a tape. A temperature of the mold was slowly increased from 25° C. to 120° C. at a rate of 5° C./min, and polymerization was performed at 120° C. for 18 hours. After the polymerization was completed, the mold was separated, followed by further curing the product at 120° C. for 4 hours to manufacture a lens sample.

2) The polythiol compositions of the examples and comparative examples were received so as to contain 49.0 wt. parts of the tetrafunctional polythiol of Preparative Example 2. Then, the received composition was uniformly admixed with 51.0 wt. parts of xylene diisocyanate, 0.01 wt. parts of dibutyltin chloride, and 0.1 wt. parts of phosphoric acid ester release agent produced by ZELEC® UN Stepan Corporation. Thereafter, a defoaming process was conducted at 600 Pa for 1 hour to prepare a polymerizable composition for an optical material.

Thereafter, the composition filtered through a 3 μm Teflon filter was injected into a mold provided with a glass mold and a tape. A temperature of the mold was slowly increased from 25° C. to 120° C. at a rate of 5° C./min, and polymerization was performed at 120° C. for 18 hours. After the polymerization was completed, the mold was separated followed by further curing the product at 120° C. for 4 hours to manufacture a lens sample.

Experimental Examples

(1) Evaluation of Stria

As described above, a lens sample having a diameter of 75 mm and −4.00 D was prepared using the polymerizable composition according to each of the examples and comparative examples. A light from a mercury lamp light source was transmitted through the prepared lens sample, and the transmitted light was projected on a white plate to determine the presence or absence of stria according to the presence or absence of contrast. Standards for evaluation are as follows.

○: Stria not observed

Δ: Fine partial stria observed x: Stria clearly observed visually (2) Evaluation of White Turbidity of the Lens For the lens samples of the examples and comparative examples prepared as described above, each sample was irradiated with right beams from a projector in a dark room, and it was visually confirmed whether the lens had haze or an opaque material.

Standards for evaluation are as follows.

○: No haze

Δ: Partial haze observed x: Haze clearly observed as a whole (3) Measurement of Polymerization Reaction Rate (Reactivity Slope)

Using a non-contact viscometer of EMS-1000 (KEM), the standard viscosity (Standard cps) was first confirmed with a viscosity standard solution (Brookfield, 1000 cps, 25° C.). Thereafter, the viscosity was measured at 10° C. for 24 hours for the polymerizable compositions according to the examples and comparative examples, respectively. Using the measured values, mathematical formulation ("mathematization") was conducted with an X-axis as a time and a Y-axis as a viscosity while converting the Y-axis in a logarithmic scale as shown in Equation 1 below, and then the reaction rate was derived therefrom.

$$Y=a \times exp(b \times X) \quad \text{[Equation 1]}$$

In Equation 1, 'a' value represents an initial viscosity (cps) while 'b' value represents the reaction rate, the measured value was expressed by rounding to the two decimal places of the measured value.

(4) Measurement of Glass Transition Temperature (Tg)

The glass transition temperature (Tg) of the lens samples of the examples and comparative examples was measured using a penetration method (load: 50 g, pin tip diameter: Φ 0.5 mm, and heating rate: 10° C./min) by using a thermomechanical analyzer (TMA Q400, TA instruments).

Evaluation results are shown together in Table 1 below.

TABLE 1

| | | Second polythiol compound | | | Properties of lens | | | |
|---|---|---|---|---|---|---|---|---|
| | First polythiol compound | Compound (A) (ppm) | Compound (B) (ppm) | Total (A + B) (ppm) | Stria | White turbidness | Reaction rate | Tg (° C.) |
| Example 1 | Preparative | 500 | 0 | 500 | ○ | ○ | 0.35 | 90 |
| Example 2 | Example 1 | 0 | 500 | 500 | ○ | ○ | 0.34 | 91 |
| Example 3 | (Trifunctional) | 500 | 500 | 1000 | ○ | ○ | 0.30 | 92 |
| Example 4 | | 5000 | 5000 | 10000 | ○ | ○ | 0.28 | 93 |
| Example 5 | | 10000 | 10000 | 20000 | ○ | ○ | 0.26 | 95 |
| Example 6 | | 400 | 100 | 500 | ○ | ○ | 0.35 | 90 |
| Example 7 | | 100 | 400 | 500 | ○ | ○ | 0.33 | 92 |
| Example 8 | | 250 | 250 | 500 | ○ | ○ | 0.35 | 91 |
| Example 9 | | 15000 | 5000 | 20000 | ○ | ○ | 0.24 | 94 |
| Example 10 | | 5000 | 15000 | 20000 | ○ | ○ | 0.24 | 96 |
| Example 11 | Preparative | 10000 | 10000 | 20000 | ○ | ○ | 0.20 | 106 |
| Example 12 | Example 1 | 500 | 0 | 500 | ○ | ○ | 0.20 | 104 |
| Example 13 | (Tetrafunctional) | 0 | 500 | 500 | ○ | ○ | 0.20 | 104 |
| Comparative Example 1 | Preparative Example 1 (Trifunctional) | — | — | — | Δ | ○ | 0.38 | 87 |
| Comparative Example 2 | Preparative Example 1 (Tetrafunctional) | — | — | — | ○ | ○ | 0.20 | 101 |
| Comparative Example 3 | Preparative Example 1 | 350 | 0 | 350 | Δ | ○ | 0.37 | 88 |
| Comparative Example 4 | (Trifunctional) | 0 | 350 | 350 | Δ | ○ | 0.37 | 89 |
| Comparative Example 5 | | 200 | 200 | 400 | Δ | ○ | 0.37 | 88 |
| Comparative Example 6 | | 10500 | 10500 | 21000 | ○ | x | 0.22 | 97 |
| Comparative Example 7 | | 5000 | 20000 | 25000 | ○ | x | 0.21 | 98 |
| Comparative Example 8 | | 20000 | 5000 | 25000 | ○ | x | 0.21 | 97 |

Referring to Table 1, a lens with reduced white turbidity phenomenon and improved mechanical properties due to an increase in the glass transition temperature while preventing stria phenomenon was manufactured through the polythiol compositions or polymerizable compositions of the examples including the second polythiol compound in the predetermined content range described above.

On the other hand, when compared with Examples 11 to 13 using the tetrafunctional polythiol compound as the first polythiol compound, it can be confirmed that, in Examples 1 to 10 using the trifunctional compound, stria and white turbidity were more clearly improved than the comparative examples using other trifunctional polythiol compounds.

What is claimed is:

1. A polythiol composition, comprising:

a first polythiol compound; and a second polythiol compound which has a molecular weight greater than that of the first polythiol compound and the number of functional groups greater than or equal to the number of functional groups of the first polythiol compound, and wherein a content of the second polythiol compound is 500 ppm to 20,000 ppm based on a weight of the first polythiol compound.

2. The polythiol composition according to claim 1, wherein the first polythiol compound includes a trifunctional polythiol compound, and the second polythiol compound includes a tetrafunctional polythiol compound.

3. The polythiol composition according to claim 1, wherein the first polythiol compound includes at least one selected from the group consisting of a trifunctional polythiol compound represented by Formula 1 and tetrafunctional polythiol compounds represented by Formulae 2-1 to 2-3:

[Formula 1]

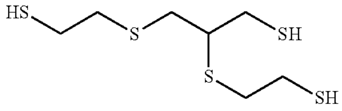

[Formula 2-1]

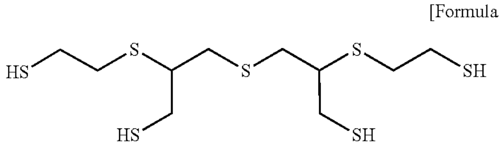

[Formula 2-2]

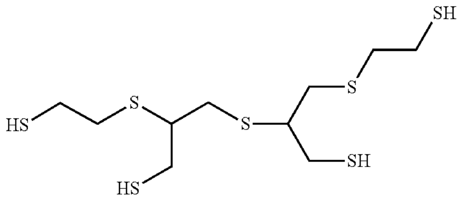

[Formula 2-3]

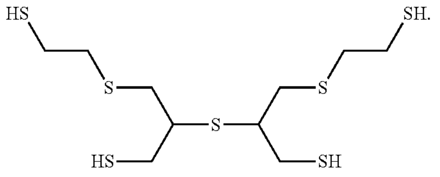

4. The polythiol composition according to claim 1, wherein the second polythiol compound includes a compound represented by $C_{12}H_{26}S_8$.

5. The polythiol composition according to claim 4, wherein the second polythiol compound includes at least one of a compound represented by Formula 3-1 and a compound represented by Formula 3-2:

[Formula 3-1]

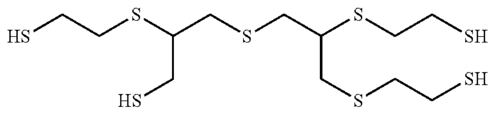

[Formula 3-2]

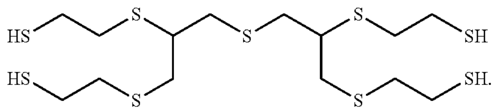

6. The polythiol composition according to claim 5, wherein the second polythiol compound includes the compound represented by Formula 3-1 and the compound represented by Formula 3-2 in a content of 500 ppm to 10,000 ppm, respectively.

7. The polythiol composition according to claim 1, wherein a content of the second polythiol compound is 1,000 ppm to 20,000 ppm.

8. A polymerizable composition for an optical material, comprising:

a first polythiol compound;

a second polythiol compound which has a molecular weight greater than that of the first polythiol compound and the number of functional groups greater than or equal to the number of functional groups of the first polythiol compound; and an isocyanate-based compound, wherein a content of the second polythiol compound is 500 ppm to 20,000 ppm based on a weight of the first polythiol compound.

9. The polymerizable composition for an optical material according to claim 8, wherein the second polythiol compound includes a compound represented by $C_{12}H_{26}S_8$.

10. The polymerizable composition for an optical material according to claim 9, wherein the second polythiol compound includes at least one of a compound represented by Formula 3-1 and a compound represented by Formula 3-2:

[Formula 3-1]

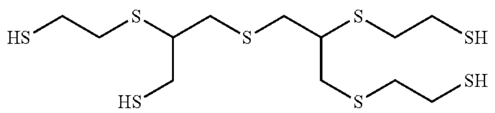

[Formula 3-2]

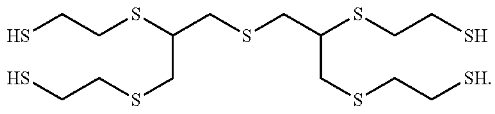

11. The polymerizable composition for an optical material according to claim 8, wherein the first polythiol compound includes a trifunctional polythiol compound.

12. The polymerizable composition for an optical material according to claim 11, wherein the first polythiol compound includes a compound represented by Formula 1:

[Formula 1]

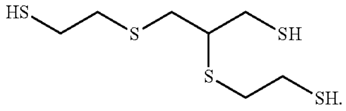

13. An optical product comprising:

a polythiourethane resin in which a polythiol compound and an isocyanate-based compound are polymerized, wherein the polythiol compound comprises a first polythiol compound, and a second polythiol compound which has a molecular weight greater than that of the first polythiol compound and the number of functional groups greater than or equal to the number of functional groups of the first polythiol compound;

wherein a content of the second polythiol compound is 500 ppm to 20,000 ppm based on a weight of the first polythiol compound.

14. The optical product according to claim 13, wherein the second polythiol compound includes a compound represented by $C_{12}H_{26}S_8$.

15. The optical product according to claim 13, wherein the optical product has a refractive index of 1.56 to 1.78.

* * * * *